United States Patent [19]

Lee

[11] Patent Number: 5,487,384
[45] Date of Patent: Jan. 30, 1996

[54] KINEMATIC ASSAY OF PLASMA GLUCOSE CONCENTRATION WITHOUT BLOOD SAMPLING

[75] Inventor: Jung J. Lee, Albany, N.Y.

[73] Assignee: Blue Marble Research, Inc., Albany, N.Y.

[21] Appl. No.: 272,317

[22] Filed: Jul. 8, 1994

Related U.S. Application Data

[63] Continuation of Ser. No. 22,974, Feb. 25, 1993, abandoned.

[51] Int. Cl.$^6$ .................................................. A61B 5/00
[52] U.S. Cl. ........................... 128/633; 128/664; 128/665
[58] Field of Search .................................... 128/630, 633, 128/664, 665

[56] References Cited

U.S. PATENT DOCUMENTS

| | | | |
|---|---|---|---|
| 4,120,755 | 10/1978 | Pierre et al. | 193/103.56 |
| 4,882,492 | 11/1989 | Schlager | 128/633 |
| 5,070,874 | 12/1991 | Barnes et al. | 128/633 |
| 5,077,476 | 12/1991 | Rosenthal | 128/633 |
| 5,101,825 | 4/1992 | Gravenstein et al. | 128/637 |
| 5,127,406 | 7/1992 | Yamaguchi | 128/633 |
| 5,178,142 | 1/1993 | Harjunmaa et al. | 128/633 |
| 5,193,543 | 3/1993 | Yelderman | 128/633 |
| 5,402,779 | 10/1995 | Chen et al. | 128/633 |

FOREIGN PATENT DOCUMENTS 1421302   9/1988   U.S.S.R. .

OTHER PUBLICATIONS

Vander et al, "Human Physiology" 1985 p. 513.
Ivan Amato, "Race Quickens for Non–Stick Blood Monitoring Technology", 258 SCIENCE 892 (Nov. 6, 1992).
E. L. Smith et al., Principles of Biotechnology: General Aspects, at 304 (7th Ed. 1983).
I. Tinoco et al., Physical Chemistry: Principles and Applications in Biological Sciences, at 282 (2nd Ed. 1985).
G. M. London, Organic Chemistry, at 1387 (1984).
Thomas J. Wheeler and Peter C. Hinkle, "The Glucose Transporter of Mammalian Cells", 47 Ann. Rev. Physiol. 503–17 (1985).
A. G. Gilman et al., The Pharmacological Basis of Therapeutics, at 1495, 1504 (7th Ed. 1985).

Primary Examiner—Angela D. Sykes
Assistant Examiner—Eric F. Winakur
Attorney, Agent, or Firm—James Creighton Wray

[57] ABSTRACT

A method is described which can identify the plasma glucose optical signal from the high background in a "total finger spectrum" by causing changes in the signal upon altering glucose concentration by administering a glucose-specific drug such as insulin, and also determine the original concentration by measuring the rate of the change as a first order kinetic dependent on the initial concentration.

13 Claims, No Drawings

KINEMATIC ASSAY OF PLASMA GLUCOSE CONCENTRATION WITHOUT BLOOD SAMPLING

This application is a continuation of U.S. Pat. Ser. No. 08/022,974 filed Feb. 25, 1993 now abandoned.

BACKGROUND OF THE INVENTION

The objective of this invention is to facilitate the measurement of the blood plasma glucose contents without having to puncture a finger to obtain a blood sample.

Various blood components can be detected by near-Infra Red(IR) beam directed to a finger. The problem is the near impossibility of distinguishing the signal of glucose from the rest of the multitudes of similar signals.

The novel idea of this invention is a practical method to 1) identify the optical absorption band of in vivo glucose by imposing a perturbation in its signal(make it move, thus kinematic) by administering a hypoglycemic drug, e.g., insulin, as well as 2) determine the initial glucose concentration from the rate of decrease of plasma glucose concentration.

This is based on the principle that the rate of transport of the plasma glucose into the cells due to insulin or any hypoglycemic drug is proportional to the initial concentration of the plasma glucose, i.e., the higher the plasma glucose concentration, the faster the transport, and thus the faster disappearance from the plasma(first order kinetic). The signal decrease is measured over a period of time(a few minutes) and the rate is fed into a computer. From the integrated form of this first order kinetic of disappearance, the initial concentration of the insulin-specific glucose is determined.

SUMMARY OF THE INVENTION

The plasma glucose concentration is determined by puncturing and taking a blood sample(Stick method). This may sound like a simple procedure. On the contrary, the puncturing causes a substantial psychological trauma especially in juvenile patients with Insulin-Dependent Diabetis Mellitus. Also, the repeated skin trauma can cause physical trauma in sensitive individuals and also the available space on the fingers is curtailed by frequent puncturing.

With the progress in non-invasive optical imaging of complex human anatomy, determination of the plasma glucose level by a non-puncturing approach(Non-Stick method) should be possible. There is a rush to measure the plasma glucose level without puncturing the skin using the near-IR optical source(1).

The crux of the problem has been the resolution of the near-IR signal associated with glucose from the mixture of similar signals from the multitudes of other components(1). The total signal intensity at a given wavelength is the sum of all contributing signals, and this can be resolved algebraically by peeling off the overlapping spectra.

In theory, such composite spectra may be resolved by studying the components in vitro. In reality, the composite spectra through finger, for example, involve many other components besides the sugars.

DETAILED DESCRIPTION OF THE INVENTION

The aim of this invention is to ameliorate this confounding problem by using a kinematic approach rather than the static. When insulin is administered, the plasma glucose level falls immediately because glucose is transported into various types of cells. This transport is facilitated by the transporter proteins in the cell membrane which are specific for D-glucose(each transporter can translocate about 500 glucose molecules). The facilitated diffusion of plasma glucose into the cells is driven only by the concentration gradient of the plasma glucose without requiring an external energy supply such as ATP(2).

In other words, the higher the plasma glucose concentration, the faster the rate of the transport into the cells, i.e., the glucose level will fall faster when the plasma glucose concentration is higher. The rate of glucose transport into the cells, dc/dt, which is equal to the rate of the disappearance of glucose from the plasma, is proportional to its concentration in the plasma, c(3);

$$-dc/dt = kc$$

where t is the time in seconds or minutes(the half-life of insulin in the human plasma is less than nine minutes), and k is a kinetic constant. Separating the variables and integrating, $\ln c = -kt + \text{constant}$; at $t=0$, $c=c_o$, and $\ln c = \ln c_o$, and $\ln (c/c_0) = -kt$, and $c = c_o e^{-kt}$ and $c_o = c/e^{-kt}$

EXAMPLE

How to identify the glucose signal and how to convert it to Non-Stick glucose concentration constitute the novelties of this invention.

How to Identify the Glucose Signal

Using a state-of-the-art portable machine equipped with a near-IR light source(1) or any other suitable excitation source, its detection system and data analyzer, the patient inserts a sample such as a finger in a fixed position into the machine and turns it on. This will allow the recording of the total basal spectrum. Then an appropriate amount of insulin(to be discussed later) is injected and the timer is started. The machine records the decreasing intensity of the particular peak or even a valley in the composite spectrum. Only this changing signal(kinematic signal) is associated with the insulin-responsive, in vivo glucose.

Identification of the Initial Base Value of Glucose Band Intensity

The glucose disappearance assumes a pseudo-linear curve initially and then reaches a plateau. Using a computer algorism for multipeak resolution(this is a well-known art), the computer follows the signal decrease (I) and plots the changes on a semilog scale as a function of time. The ln I vs. t plot yields a straight line. This line is interpolated to the zero time to obtain $\ln I_0(3)$, and the original signal intensity. Only this way, the identity of the initial signal associated with glucose can be validated. This interpolated value may or may not coincide with the first baseline spectrum value since the composite intensity will depend on how complex the patient's system is at that particular moment.

Determination of the Rate Constant

The insulin-specific, decreasing peak is identified, and the initial intensity is determined thus far. A plot of $\ln I_o/I$ vs. t gives a straight line with a positive slope which is the first order rate constant, k(per unit time). Since the ratio of the two concentrations is used, the unit of the concentration is irrelevant, and the ratio of any signal can be used directly, namely, the baseline signal before insulin($I_o$) and the remaining intensity of the signal at each time point, I(t).

Theoretically only a two-point measurement may suffice within a few minutes or so after insulin injection(the half-life of insulin in humans is less than nine minutes). Knowing the ratio of the intensities, the times of measurements, and the rate constant, the computer can calculate any signal intensity through the proportionality relationship given above.

Conversion of the signal intensity into a concentration unit of glucose per unit volume of blood plasma can be achieved in several ways:

From in vitro Values

Since the signal is attributable only to glucose, such a signal determined for pure glucose in vitro may be used. If a polarimetry was used as a detector, this approach can become realistic.

From Model Systems

The manufacturer of the machine can provide the conversion factor. The near-IR absorption spectra of glucose, which exists in solution primarily as D-glucopyranose stereoisomers(4), through a finger may be approximated by injecting glucose into a rabbit and determining the proportionate signal increase in the animal through the skin as a function of injected amounts. The identity of this signal with glucose should be verified by causing its decrease by insulin injection and also non-perturbation by injection of transport inhibitors such as forskolin(5). At the same time points of the optical intensity measurements, blood samples are taken(from the ear artery) and the Stick-c's are determined, say, in mMole glucose per deciliter. The signal intensity divided by the corresponding Stick-c gives the conversion factor, in absorptivity per mMole glucose per deciliter(per millimeter finger path). Knowing the intensity and the intensity-concentration conversion factor, any signal can be converted to concentration by the analyzer. This animal model conversion factor may be adjusted to human factors by comparing it with results from human volunteers.

Another approach is that the instrument manufacturer compiles a comprehensive table of the rate constants from volunteer patients with a broad range of original plasma glucose concentrations, and since a machine user can obtain his/her own rate constant after an insulin injection as described above, the user enters the kinetic constant and the time of measurements(and the amount of insulin used) into the machine, and the computer can pick out the corresponding initial Non-Stick glucose concentration from a table of the intensities at a specified time and the kinetic constants for a given amount of insulin used.

From Each Individual

The most practical and probably most meaningful way is to determine the conversion factor for the Non-Stick c from the Stick c of each individual when the machine is purchased and store that data into the computer as a conversion factor. With the assistance of personnel from the machine manufacturer or by a physician, the first recordings of the insulin-dependent glucose signal changes should be parallelled by two or more points of Stick c determinations. The net change in the signal intensity per net time change divided by the net change in the Stick-glucose concentration change over this time period gives the conversion factor of, for example, the absorptivity per mMole glucose per deciliter blood. Such an initial testing would serve not only to get the individual familiarized with the machine but also establish a "calibration test" for each individual's insulin needs. The known maintenance insulin injection and concomitant Non-Stick c determination should suffice as the daily monitor. Should this result indicate a higher than daily level, then additional insulin may be indicated. Insulin injection is less traumatic than the blood-letting. Or, if there is a cause for alarm, a physician should be consulted.

It may be borne in mind that Stick c is determined by glucose oxidase which is specific for glucose whereas insulin causes the transport of some other hexoses also(as well as some mineral ions) in addition to glucose. Thus, the Stick c itself is already a relative parameter as far as insulin efficacy is concerned. Therefore, until the exact nature of the insulin action becomes known, the absorptivity of the kinematic band appears to serve as the best assay.

This method is not restricted to insulin. In Non-Insulin-Dependent Diabetis Mellitus, other functions than insulin synthesis are inhibited(6), and various drugs specific to each dysfunction are used. Thus, this method is useful, in like manner, with the administration of other drugs.

There are other important applications of this kinematic approach: The amount of a drug in the plasma or a tissue can be very different from the amount administered. Classically, the amount delivered is measured by the amount recovered in urine which is not only time consuming but also is subject to metabolic enzyme functions. This method can determine the amount of drug delivered into the plasma by measuring the optical signal through the skin that increases after a drug administration as a function of time. Conversely, the efficacy of drugs such as insulin can be monitored by individuals by this method: for example, the kinematic constant may show a large deviation in individuals with other dysfunctions than the presumed, and thus serve as a diagnostic constant.

It is envisioned that fibre optics pressed into a sensitive point in a tissue, or inserted into the injecting syringe may simultaneously serve to "listen" to a changing signal after a drug adminisration. For example, in the case of insulin, the appreciable lowering of glucose concentration would produce a decrease in the osmotic pressure of the plasma(an extreme example is insulin shock). Such changes in the pressure can be converted to the glucose concentration via a pressure transducer. Currently, the mechanisms of cellular functions and pathogenesis are explored actively in terms of the signal transduction at the cell surface membrane and generation of the cellular messengers. Some of the general messengers are species such as calcium ion, measurable with electrochemical potential change, and free radicals, notably superoxide and nitric oxide, measurable with electron paramagnetic resonance. Such physico-chemical changes could be monitored by devices similar to a portable telephone in the future.

We are investigating more appropriate anatomical parts for each function to be monitored—for example, for a transmission signal, auricular(ear) arteries may enhance signal measurements.

It is further envisioned that this type of kinematic method may facilitate the monitoring of chronic diseases in which the disease progression is slow so that the patient is entrusted to home care environments. Administration of a "chronic drug" (possibly tagged with a tracer) and the measurement of the ensuing rate of change in the plasma drug concentration, the disease-associated parameters, such as, for example, protein production associated with AIDS or Alzheimer's disease, or hormones, for example in cancer patients in remission, would facilitate the otherwise difficult measurements non-invasively, and provide a direct indicator of the efficacy of a drug as well as the disease prognosis.

I claim:

1. A method for the determination of an in vivo glucose concentration without blood sampling comprising the steps of:

(a) directing a beam of light to a body part of a patient;

(b) administering a hypoglycemic drug to the patient to impose a kinematic perturbation in the in vivo glucose concentration;

(c) identifying an optical absorption band of in vivo glucose measuring an intensity of a glucose signal;

(d) measuring a rate of decrease of the intensity of the glucose signal with time;

(e) determining an original glucose signal from the rate of decrease measured and (f) converting the original signal into an original in glucose concentration.

2. The method of claim 1, wherein the step of administering the hypoglycemic drug includes the step of administering insulin.

3. A method for identifying instrumental signals associated with in situ cellular components and measuring in vivo a concentration of the components comprising the steps of:

(a) administering to a patient a compound specific for the component to be measured, wherein the compound imposes a kinematic perturbation which changes the in vivo concentration of the component specific for the component to be measured;

(b) measuring a rate of change of the in vivo concentration of the component;

(c) and determining the original in vivo concentration of the component from the rate of change measured.

4. A method for determining in vivo glucose concentrations without blood sampling comprising the steps of:

(a) detecting an intensity of glucose signals non invasively by projecting energy through a body part of a patient and detecting energy received through the body part;

(b) administering a hypoglycemic drug to the patient (c) sequentially detecting changes in the intensity of the glucose signals;

(d) measuring a rate of changing intensity of the sequentially detected glucose signals; and (e) determining an original glucose concentration from the measured rate of changing intensity.

5. The method of claim 4, wherein the step of administering the hypoglycemic drug includes the step of administering insulin.

6. A method for the determination of in vivo glucose concentrations without blood sampling comprising the steps of:

(a) administering a hypoglycemic drug to a patient;

(b) projecting light through a body part of the patient, measuring a decreasing optical spectrum at subsequent time intervals to obtain difference spectra, and identifying a peak absorbance position of the in vivo glucose from the difference spectra corresponding to the decreasing glucose concentration;

(c) plotting changing peak absorbances on a logarithmic axis versus time on a linear abscissa (semi-log plot) to obtain a straight line;

(d) interpolating the straight line with a negative slope to the axis logarithmic at time zero for obtaining an original pure glucose absorbance;

(e) comparing the original glucose absorbance against a reference table comprising a column of original glucose absorbance values matched with pre-determined blood glucose concentrations determined by a blood sampling method before administration of the hypoglycemic drug;

(f) and determining the original glucose concentration from the comparing step.

7. The method of claim 6, wherein the step of administering the hypoglycemic drug includes the step of administering insulin.

8. The method of claim 6, wherein the the step of administering the hypoglycemic drug includes the step of administering a palliative causing change in blood glucose concentration.

9. A method for identifying instrumental signals in in-vivo cellular components and measuring an in vivo concentration of the components comprising the steps of:

(a) administering a compound to a patient specific for a component to be measured that causes changes in the in vivo concentration of the component;

(b) projecting energy through a body part of the patient and detecting energy received through the body part to measure differential changes in intensity of a spectrum over a time period to obtain an identity of a peak position of the component;

(c) plotting the changes in intensity of the peak position on an appropriate scale in a semi-log plot to obtain a line;

(d) interpolating the obtained line to an original intensity at a time before the administering of the compound to obtain an original pure component intensity;

(e) matching the so obtained original pure component intensity against a reference table constructed by collection of data obtained by measuring concentration through blood sampling before administration of the compound.

10. A method for determining in vivo glucose concentrations comprising the steps of:

(a) identifying a glucose signal by administration of a hypoglycemic drug, finding a changing intensity signal and interpreting the changing intensity signal as a decreasing glucose signal;

(b) obtaining a first order kinetic analysis of the decreasing glucose signal to obtain a kinetic constant from a slope of a semi-log plot for storing in a database for a diagnostic purpose.

11. A method for identifying in vivo glucose signals blood sampling comprising the steps of:

(a) administering a hypoglycemic drug to a patient;

(b) obtaining with respect to a time a changing glucose signal to identify a pure glucose spectrum and its peak intensity;

(c) plotting the changing peak intensity on an appropriate plot in a first order or semi-log kinetic plot;

(d) interpolating a straight line to an origin at time zero to obtain an original in vivo blood plasma glucose concentration.

12. The method of claim 11, wherein the step of administering the hypoglycemic drug is includes the step of administering insulin.

13. The method of claim 11, wherein the step of administering the hypoglycemic drug includes the step of administering a palliative.

\* \* \* \* \*

UNITED STATES PATENT AND TRADEMARK OFFICE
CERTIFICATE OF CORRECTION

PATENT NO. : 5,487,384
DATED : January 30, 1996
INVENTOR(S) : Jung Ja Lee It is certified that error appears in the above-identified patent and that said Letters Patent is hereby corrected as shown below:

On the title page, under Item [56] OTHER PUBLICATIONS:

line 4, change "Biotechnology" to --Biochemistry--;

line 8, change "London" to --Loudon--.

Column 5, line 6, after the first "glucose" add --and--;

line 13, before "glucose" insert --vivo--;

line 61, change "axis logarithmic" to --logarithmic axis--.

Column 6, line 47, before "blood" insert --without--;

line 59, delete "is".

Signed and Sealed this

Twenty-third Day of July, 1996

*Attest:*

BRUCE LEHMAN

*Attesting Officer*      *Commissioner of Patents and Trademarks*